(12) United States Patent
Den Boef et al.

(10) Patent No.: US 8,908,147 B2
(45) Date of Patent: Dec. 9, 2014

(54) METHOD AND APPARATUS FOR DETERMINING AN OVERLAY ERROR

(75) Inventors: Arie Jeffrey Den Boef, Waalre (NL); Maurits Van Der Schaar, Eindhoven (NL); Andreas Fuchs, Meerbusch (DE); Martyn John Coogans, Eindhoven (NL); Kaustuve Bhattacharyya, Veldhoven (NL); Stephen Peter Morgan, Son en Breugel (NL); Michael Kubis, Dresden (DE)

(73) Assignee: ASML Netherlands B.V., Veldhoven (NL)

( * ) Notice: Subject to any disclaimer, the term of this patent is extended or adjusted under 35 U.S.C. 154(b) by 564 days.

(21) Appl. No.: 13/181,932

(22) Filed: Jul. 13, 2011

(65) Prior Publication Data

US 2012/0013881 A1  Jan. 19, 2012

Related U.S. Application Data

(60) Provisional application No. 61/365,538, filed on Jul. 19, 2010.

(51) Int. Cl.
| | | |
|---|---|---|
| *G03F 7/20* | (2006.01) | |
| *A01H 1/06* | (2006.01) | |
| *G03B 27/52* | (2006.01) | |
| *G03B 27/53* | (2006.01) | |
| *A01G 1/00* | (2006.01) | |
| *C12N 15/82* | (2006.01) | |

(52) U.S. Cl.
CPC *A01H 1/06* (2013.01); *G03B 27/52* (2013.01); *G03B 27/53* (2013.01); *G03F 7/705* (2013.01); *G03F 7/70633* (2013.01); *A01G 1/001* (2013.01); *C12N 15/8201* (2013.01)
USPC ................. 355/53; 355/67; 355/77

(58) Field of Classification Search
CPC . G03F 7/705; G03F 7/70608; G03F 7/70616; G03F 7/70625; G03F 7/70633; G01N 21/47; G01N 2121/4704; G01N 2121/4709; G01N 2015/0222; G01B 11/14; G01B 11/27; H01L 21/67225
USPC ......... 355/53, 67, 77; 356/337–343; 702/150; 430/16
See application file for complete search history.

(56) References Cited

U.S. PATENT DOCUMENTS 5,877,036 A * 3/1999 Kawai .............................. 438/16
5,963,329 A * 10/1999 Conrad et al. ................ 356/613
(Continued)

FOREIGN PATENT DOCUMENTS

| CN | 101231472 A | 7/2008 |
|---|---|---|
| CN | 101566800 A | 10/2009 |

(Continued)

OTHER PUBLICATIONS

Chen, X., et al., "Accurate alignment on asymmetrical signals", Journal of Vacuum Science and Technology B, vol. 15, No. 6, pp. 2185-2188 (1997).

(Continued)

*Primary Examiner* — Steven H Whitesell Gordon
(74) *Attorney, Agent, or Firm* — Sterne, Kessler, Goldstein & Fox P.L.L.C.

(57) ABSTRACT

A method of determining an overlay error. Measuring an overlay target having process-induced asymmetry. Constructing a model of the target. Modifying the model, e.g., by moving one of the structures to compensate for the asymmetry. Calculating an asymmetry-induced overlay error using the modified model. Determining an overlay error in a production target by subtracting the asymmetry-induced overlay error from a measured overlay error. In one example, the model is modified by varying asymmetry $p^{(n')}$, $p^{(n'')}$ and the calculating an asymmetry-induced overlay error is repeated for a plurality of scatterometer measurement recipes and the step of determining an overlay error in a production target uses the calculated asymmetry-induced overlay errors to select an optimum scatterometer measurement recipe used to measure the production target.

20 Claims, 9 Drawing Sheets

(56) References Cited

U.S. PATENT DOCUMENTS

| | | | |
|---|---|---|---|
| 6,064,486 A * | 5/2000 | Chen et al. | 356/401 |
| 7,232,758 B2 * | 6/2007 | Chen | 438/689 |
| 7,619,737 B2 | 11/2009 | Mos et al. | |
| 2002/0137237 A1 * | 9/2002 | Byers et al. | 438/14 |
| 2002/0149782 A1 * | 10/2002 | Raymond | 356/616 |
| 2002/0158193 A1 * | 10/2002 | Sezginer et al. | 250/237 G |
| 2003/0212525 A1 | 11/2003 | Bischoff et al. | |
| 2004/0040003 A1 * | 2/2004 | Seligson et al. | 716/4 |
| 2004/0059540 A1 | 3/2004 | Matsumoto et al. | |
| 2006/0033921 A1 | 2/2006 | Den Boef et al. | |
| 2009/0168062 A1 * | 7/2009 | Straaijer | 356/364 |
| 2010/0321654 A1 * | 12/2010 | Den Boef | 355/53 |

FOREIGN PATENT DOCUMENTS

| | | |
|---|---|---|
| EP | 0 793 147 A1 | 9/1997 |
| EP | 1 628 164 A2 | 2/2006 |
| WO | WO 03/104929 A2 | 12/2003 |
| WO | WO 2010/145951 A2 | 12/2010 |
| WO | WO2012010458 A1 * | 1/2012 |

OTHER PUBLICATIONS

International Search Report with the Written Opinion of the International Searching Authority directed to related International Patent Application No. PCT/EP2011/061822, mailed Oct. 12, 2011, from the European Patent Office; 11 pages.

English-Language Abstract for Chinese Patent Publication No. 101566800 A, published Oct. 28, 2009; 1 page.

* cited by examiner

METHOD AND APPARATUS FOR DETERMINING AN OVERLAY ERROR

CROSS REFERENCE TO RELATED APPLICATIONS

This application claims benefit under 35 U.S.C. §119(e) to U.S. Provisional Application No. 61/365,538, filed Jul. 19, 2010, which is incorporated by reference herein in its entirety.

BACKGROUND

1. Field of the Present Invention

The present invention relates to methods and inspection apparatus for determining an overlay error, for example in the manufacture of devices by lithographic techniques using a lithographic apparatus.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between two layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-destructive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Semiconductor device manufacturers align wafers using gratings that are present on a wafer. An alignment sensor measures the location of a grating with sub-nm repeatability. The manufacturers also measure on-product overlay using overlapping gratings. Here sub-nm Total Measurement Uncertainty (TMU) numbers are easily achieved as well. However, overlay metrology and alignment sensors are sensitive to marker asymmetry caused by processing steps like etch, Chemical Mechanical Polishing (CMP) and deposition. These asymmetries lead to overlay and alignment errors that are of the order of a few nm's. This effect starts to dominate the overlay budget and solutions are therefore needed.

Scatterometer measurement recipe selection (for example with each recipe having various wavelengths and polarizations of illumination) is currently performed using parameters such as mean Tool Induced Shift (TIS) and or TIS variability (a.k.a. TIS 3 sigma). There is a problem when the reference layer exhibits an asymmetrical profile.

Asymmetries in the shape of a target grating will generally have an impact on the measured overlay. This impact can vary depending on the illumination setting used for the measurement.

Target recipe selection is performed without actual knowledge of the shape of the gratings after processing and imaging. Furthermore, the context of the current process is not used in the decision of recipe selection. The use of qualifiers that are based on TIS and/or TMU do not always lead to a measurement recipe that is most robust against target asymmetry.

SUMMARY

According to a first aspect of the present invention there is provided a method of determining an overlay error, the method comprising: measuring scattering properties of a first target comprising a first structure, constructing a model of the first structure using the measured scattering properties, the model comprising a first model structure corresponding to the first structure, modifying the model based on asymmetry of the first model structure, calculating an asymmetry-induced overlay error between the first model structure and a second model structure, the first and second model structures being overlaid with respect to each other in the modified model, and determining an overlay error in a second target using the calculated asymmetry-induced overlay error.

According to a second aspect of the present invention there is provided an inspection apparatus for determining an overlay error, the inspection apparatus configured to measure scattering properties of a first target comprising a first structure and the inspection apparatus comprising at least one processor configured to: construct a model of the first structure using the measured scattering properties, the model comprising a first model structure corresponding to the first structure, modify the model based on asymmetry of the first model structure, calculate an asymmetry-induced overlay error between the first model structure and a second model structure, the first and second model structures being overlaid with respect to each other in the modified model, determine an overlay error in a second target using the calculated asymmetry-induced overlay error.

According to a third aspect of the present invention there is provided a lithographic apparatus comprising: an illumination optical system arranged to illuminate a pattern, a projection optical system arranged to project an image of the pattern on to a substrate, and an inspection apparatus according to the second aspect.

According to a fourth aspect of the present invention there is provided a lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and an inspection apparatus according to the second aspect.

According to a fourth aspect of the present invention there is provided a computer program product containing one or more sequences of machine-readable instructions for determining an overlay error, the instructions being adapted to cause one or more processors to perform a method of determining an overlay error, the method comprising the steps: measuring scattering properties of a first target comprising a first structure, constructing a model of the first structure using the measured scattering properties, the model comprising a first model structure corresponding to the first structure, modifying the model based on asymmetry of the first model structure, calculating an asymmetry-induced overlay error between the first model structure and a second model structure, the first and second model structures being overlaid with respect to each other in the modified model, and determining an overlay error in a second target using the calculated asymmetry-induced overlay error.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
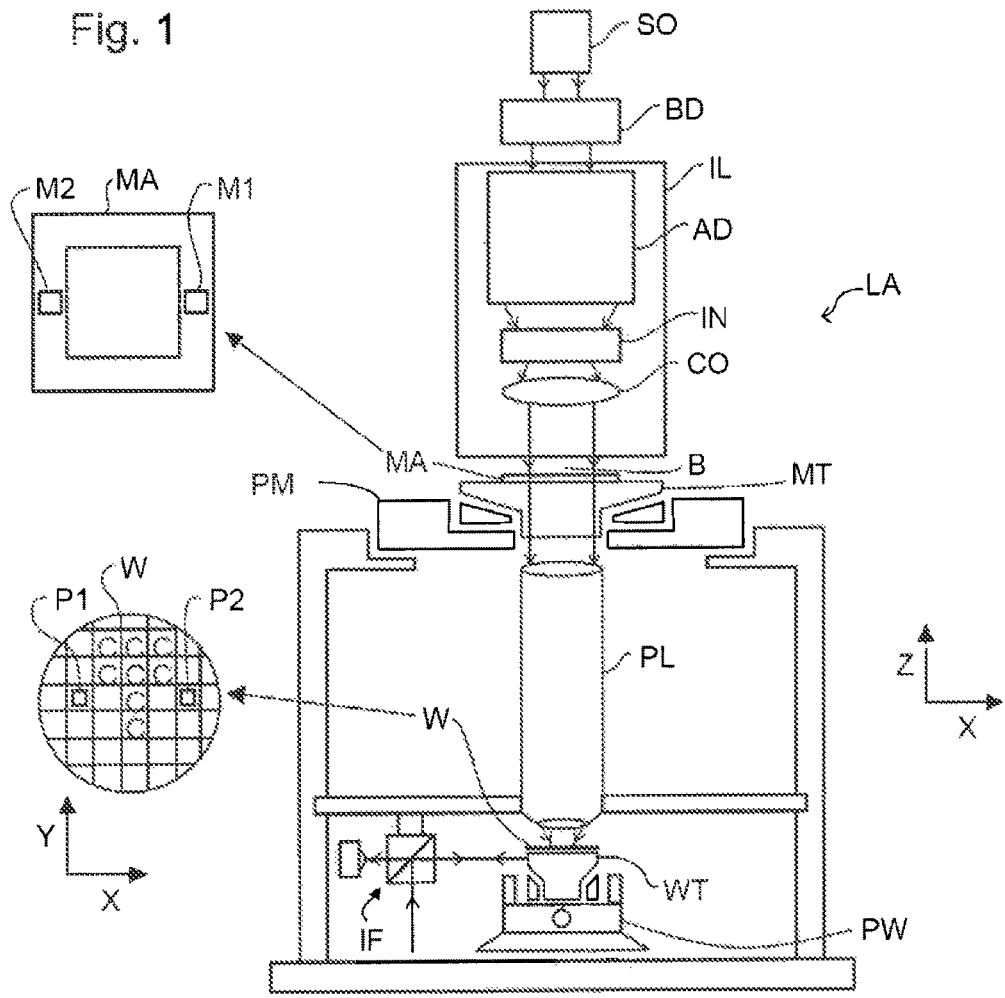
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.
2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.
3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
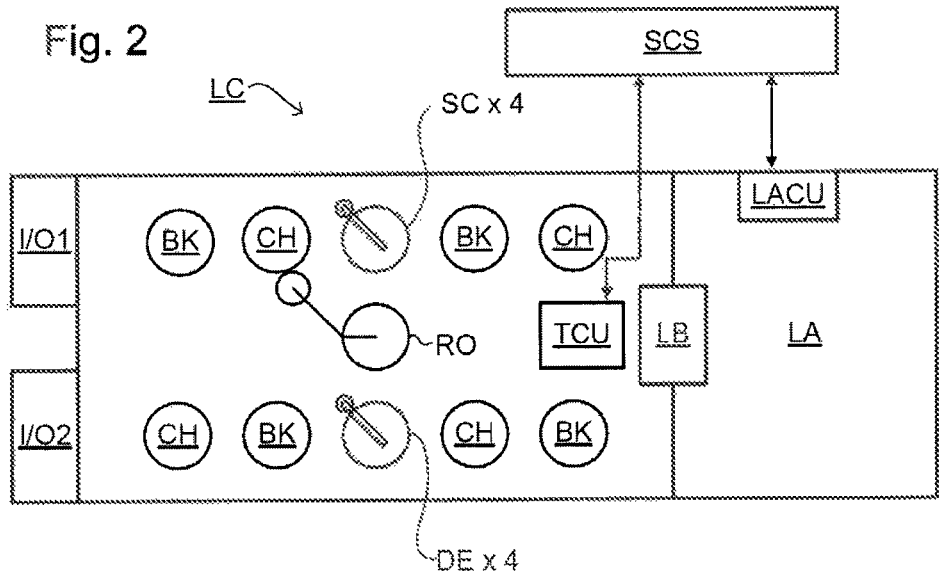
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, 1/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between two layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
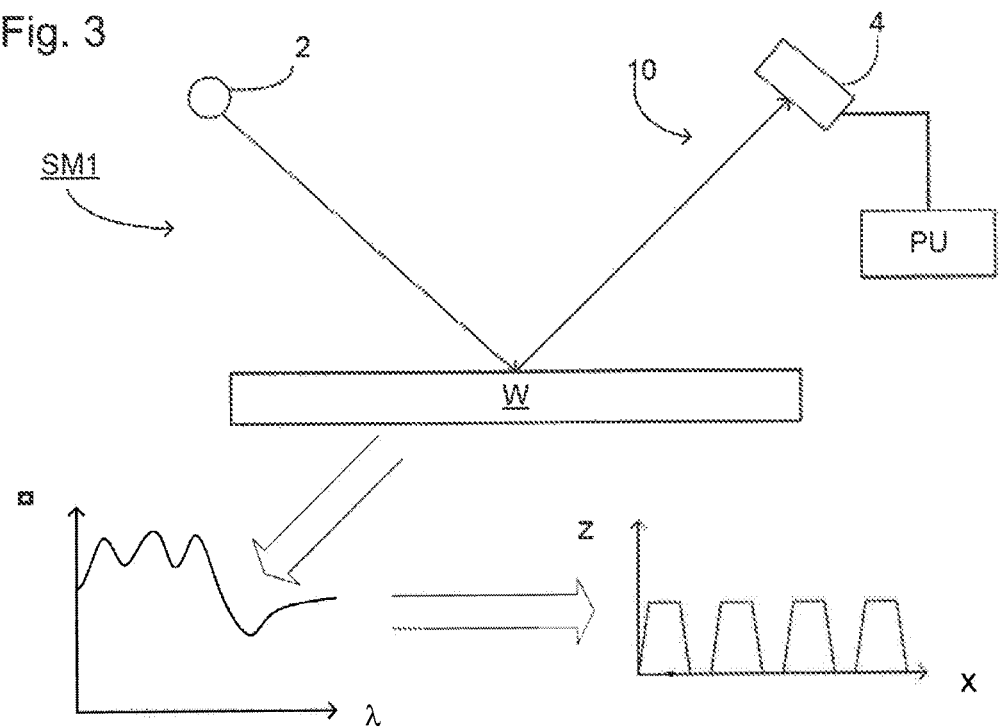
FIG. 3 depicts a first scatterometer.

FIG. 3 depicts a scatterometer which may be used in the present invention. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer. At normal incidence, however, this scatterometer has no sensitivity for pattern asymmetry. In order to detect pattern asymmetry in the 0-th diffraction order, oblique incidence is needed.

Figure 4:
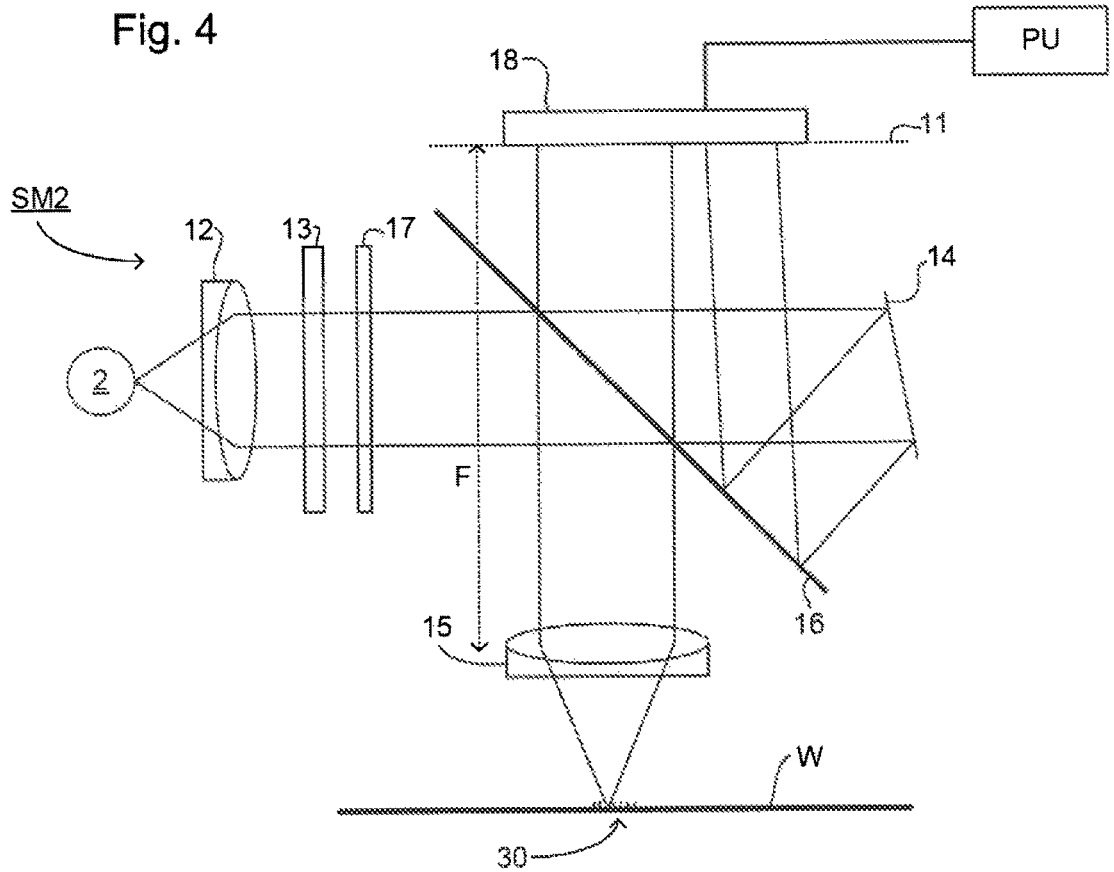
FIG. 4 depicts a second scatterometer.

Another scatterometer that is more suitable for the present invention is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein in its entirety.

The target 30 on substrate W may be a 1-D periodic grating, which is printed such that after development, the bars are formed of solid resist lines. The target 30 may be a 2-D periodic grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

As described above, the target is on the surface of the substrate. This target will often take the shape of a series of lines in a grating or substantially rectangular structures in a 2-D array. The purpose of rigorous optical diffraction theories in metrology is effectively the calculation of a diffraction spectrum that is reflected from the target. In other words, target shape information is obtained for CD (critical dimension) uniformity and overlay metrology. Overlay metrology is a measuring system in which the overlay of two targets is measured in order to determine whether two layers on a substrate are aligned or not. CD uniformity is simply a measurement of the uniformity of the grating on the spectrum to determine how the exposure system of the lithographic apparatus is functioning. Specifically, CD, or critical dimension, is the width of the object that is "written" on the substrate and is the limit at which a lithographic apparatus is physically able to write on a substrate.

Using one of the scatterometers described above in combination with modeling of a target structure such as the target 30 and its diffraction properties, measurement of the shape and other parameters of the structure can be performed in a number of ways. In a first type of process, represented by FIG. 5, a diffraction pattern based on a first estimate of the target shape (a first candidate structure) is calculated and compared with the observed diffraction pattern. Parameters of the model are then varied systematically and the diffraction re-calculated in a series of iterations, to generate new candidate structures and so arrive at a best fit. In a second type of process, represented by FIG. 6, diffraction spectra for many different candidate structures are calculated in advance to create a 'library' of diffraction spectra. Then the diffraction pattern observed from the measurement target is compared with the library of calculated spectra to find a best fit. Both methods can be used together: a coarse fit can be obtained from a library, followed by an iterative process to find a best fit.

Figure 5:
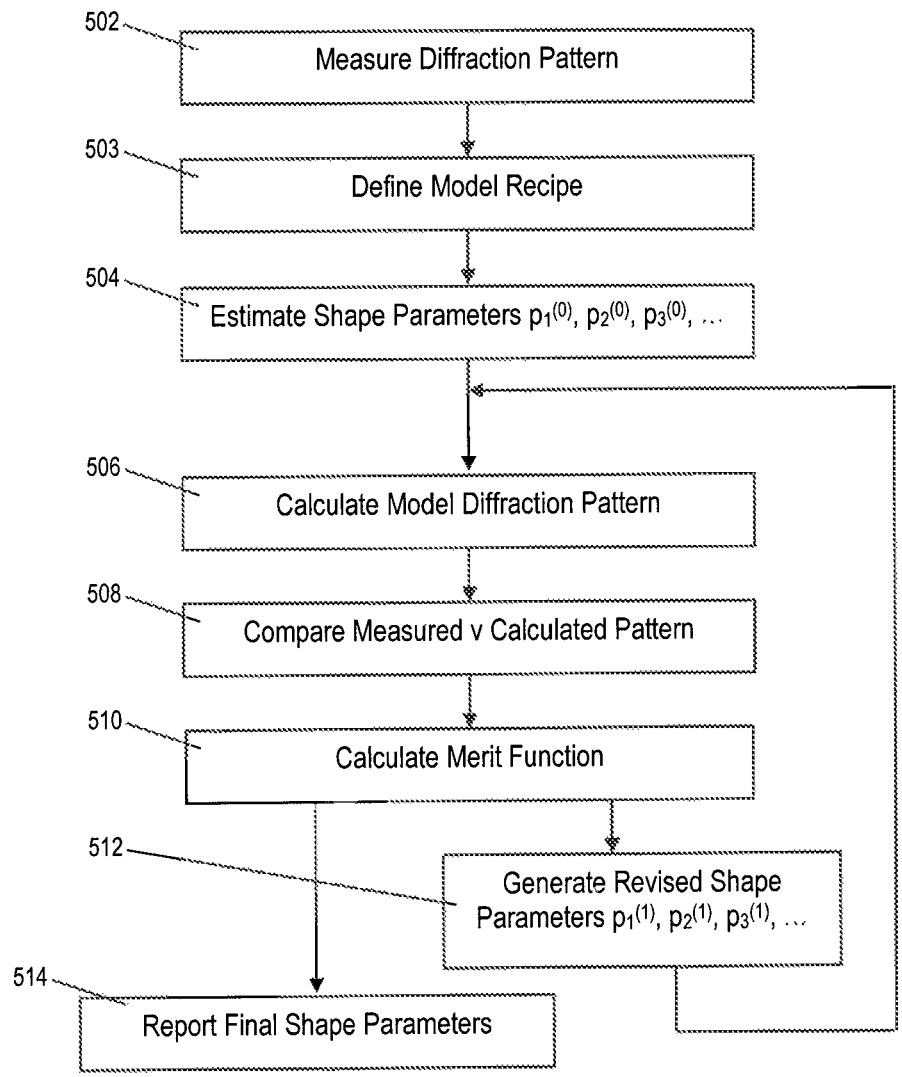
FIG. 5 depicts a first example process for reconstruction of a structure from scatterometer measurements.

Referring to FIG. 5 in more detail, the way the measurement of the target shape and/or material properties is carried out will be described in summary. The target will be assumed for this description to be periodic in only 1 direction (1-D structure). In practice it may be periodic in 2 directions (2-dimensional structure), and the processing will be adapted accordingly.

In step 502: The diffraction pattern of the actual target on the substrate is measured using a scatterometer such as those described above. This measured diffraction pattern is forwarded to a calculation system such as a computer. The calculation system may be the processing unit PU referred to above, or it may be a separate apparatus.

In step 503: A 'model recipe' is established which defines a parameterized model of the target structure in terms of a number of parameters $p_i$ ($p_1$, $p_2$, $p_3$ and so on). These parameters may represent for example, in a 1D periodic structure, the angle of a side wall, the height or depth of a feature, the width of the feature. Properties of the target material and underlying layers are also represented by parameters such as refractive index (at a particular wavelength present in the scatterometry radiation beam). Specific examples will be given below. Importantly, while a target structure may be defined by dozens of parameters describing its shape and material properties, the model recipe will define many of these to have fixed values, while others are to be variable or 'floating' parameters for the purpose of the following process steps. Further below we describe the process by which the choice between fixed and floating parameters is made. Moreover, we shall introduce ways in which parameters can be permitted to vary without being fully independent floating parameters. For the purposes of describing FIG. 5, only the variable parameters are considered as parameters $p_i$ 504: A model target shape is estimated by setting initial values $p_i^{(0)}$ for the floating parameters (i.e., $p_1^{(0)}$, $p_2^{(0)}$, $p_3^{(0)}$ and so on). Each floating parameter will be generated within certain predetermined ranges, as defined in the recipe.

In step 506: The parameters representing the estimated shape, together with the optical properties of the different elements of the model, are used to calculate the scattering properties, for example using a rigorous optical diffraction method such as RCWA or any other solver of Maxwell equations. This gives an estimated or model diffraction pattern of the estimated target shape.

In steps 508, 510: The measured diffraction pattern and the model diffraction pattern are then compared and their similarities and differences are used to calculate a "merit function" for the model target shape.

In step 512: Assuming that the merit function indicates that the model needs to be improved before it represents accurately the actual target shape, new parameters $p_1^{(1)}$, $p_2^{(1)}$, $p_3^{(1)}$, etc. are estimated and fed back iteratively into step 506. Steps 506-512 are repeated.

In order to assist the search, the calculations in step 506 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

In step 514: When the merit function indicates that this iterative process has converged on a solution with a desired accuracy, the currently estimated parameters are reported as the measurement of the actual target structure.

The computation time of this iterative process is largely determined by the forward diffraction model used, i.e., the calculation of the estimated model diffraction pattern using a rigorous optical diffraction theory from the estimated target structure. If more parameters are required, then there are more degrees of freedom. The calculation time increases in principle with the power of the number of degrees of freedom. The estimated or model diffraction pattern calculated at 506 can be expressed in various forms. Comparisons are simplified if the calculated pattern is expressed in the same form as the measured pattern generated in step 510. For example, a modeled spectrum can be compared easily with a spectrum measured by the apparatus of FIG. 3; a modeled pupil pattern can be compared easily with a pupil pattern measured by the apparatus of FIG. 4.

Throughout this description from FIG. 5 onward, the term 'diffraction pattern' will be used, on the assumption that the scatterometer of FIG. 4 is used. The skilled person can readily adapt the teaching to different types of scatterometer, or even other types of measurement instrument.

Figure 6:
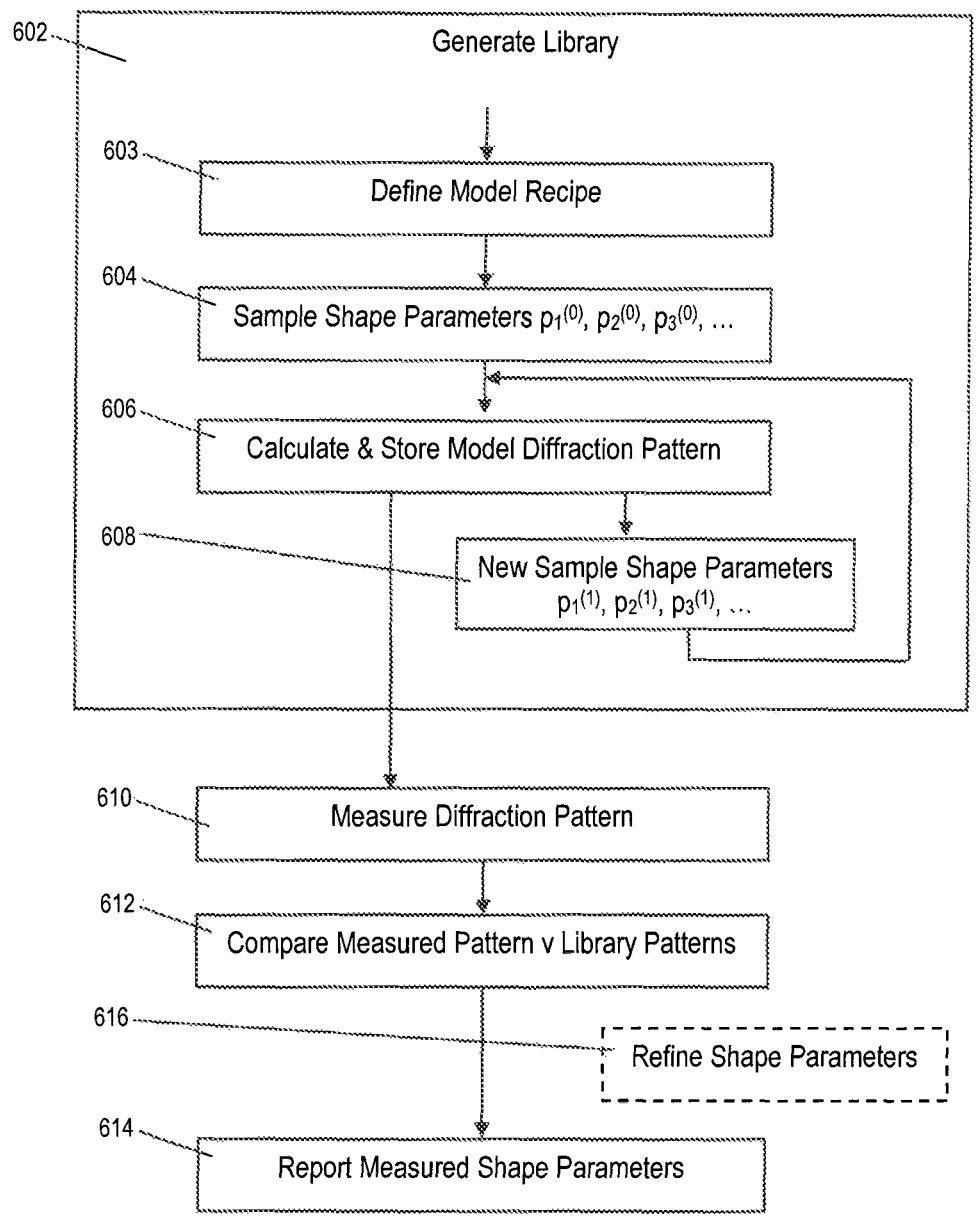
FIG. 6 depicts a second example process for reconstruction of a structure from scatterometer measurements.

FIG. 6 illustrates an alternative example process in which plurality of model diffraction patterns for different estimated target shapes (candidate structures) are calculated in advance and stored in a library for comparison with a real measurement. The underlying principles and terminology are the same as for the process of FIG. 5. The steps of the FIG. 6 process are:

In step 602: The process of generating the library begins. A separate library may be generated for each type of target structure. The library may be generated by a user of the measurement apparatus according to need, or may be pre-generated by a supplier of the apparatus.

In step 603: A 'model recipe' is established which defines a parameterized model of the target structure in terms of a number of parameters $p_i$ ($p_1$, $p_2$, $p_3$ and so on). Considerations are similar to those in step 503 of the iterative process.

In step 604: A first set of parameters $p_1^{(0)}$, $p_2^{(0)}$, $p_3^{(0)}$, etc. is generated, for example by generating random values of all the parameters, each within its expected range of values.

In step 606: A model diffraction pattern is calculated and stored in a library, representing the diffraction pattern expected from a target shape represented by the parameters.

In step 608: A new set of shape parameters $p_1^{(1)}$, $p_2^{(1)}$, $p_3^{(1)}$, etc. is generated. Steps 606-608 are repeated tens, hundreds or even thousands of times, until the library which comprises all the stored modeled diffraction patterns is judged sufficiently complete. Each stored pattern represents a sample point in the multi-dimensional parameter space. The samples in the library should populate the sample space with a sufficient density that any real diffraction pattern will be sufficiently closely represented.

In step 610: After the library is generated (though it could be before), the real target 30 is placed in the scatterometer and its diffraction pattern is measured.

In step 612: The measured pattern is compared with the modeled patterns stored in the library to find the best matching pattern. The comparison may be made with every sample in the library, or a more systematic searching strategy may be employed, to reduce computational burden.

In step 614: If a match is found then the estimated target shape used to generate the matching library pattern can be determined to be the approximate object structure. The shape parameters corresponding to the matching sample are output as the measured shape parameters. The matching process may be performed directly on the model diffraction signals, or it may be performed on substitute models which are optimized for fast evaluation.

In step 616: Optionally, the nearest matching sample is used as a starting point, and a refinement process is used to obtain the final parameters for reporting. This refinement process may comprise an iterative process very similar to that shown in FIG. 5, for example.

Whether refining step 616 is needed or not is a matter of choice for the implementer. If the library is very densely sampled, then iterative refinement may not be needed because a good match will always be found. On the other hand, such a library might be too large for practical use. A practical solution is thus to use a library search for a coarse set of parameters, followed by one or more iterations using the merit function to determine a more accurate set of parameters to report the parameters of the target substrate with a desired accuracy. Where additional iterations are performed, it would be an option to add the calculated diffraction patterns and associated refined parameter sets as new entries in the library. In this way, a library can be used initially which is based on a relatively small amount of computational effort, but which builds into a larger library using the computational effort of the refining step 616. Whichever scheme is used, a further refinement of the value of one or more of the reported variable parameters can also be obtained based upon the goodness of the matches of multiple candidate structures. For example, the parameter values finally reported may be produced by interpolating between parameter values of two or more candidate structures, assuming both or all of those candidate structures have a high matching score.

The computation time of this iterative process is largely determined by the forward diffraction model at steps 506 and 606, i.e., the calculation of the estimated model diffraction pattern using a rigorous optical diffraction theory from the estimated target shape.

The present invention relates to embodiments for determining overlay errors.

Figure 7:
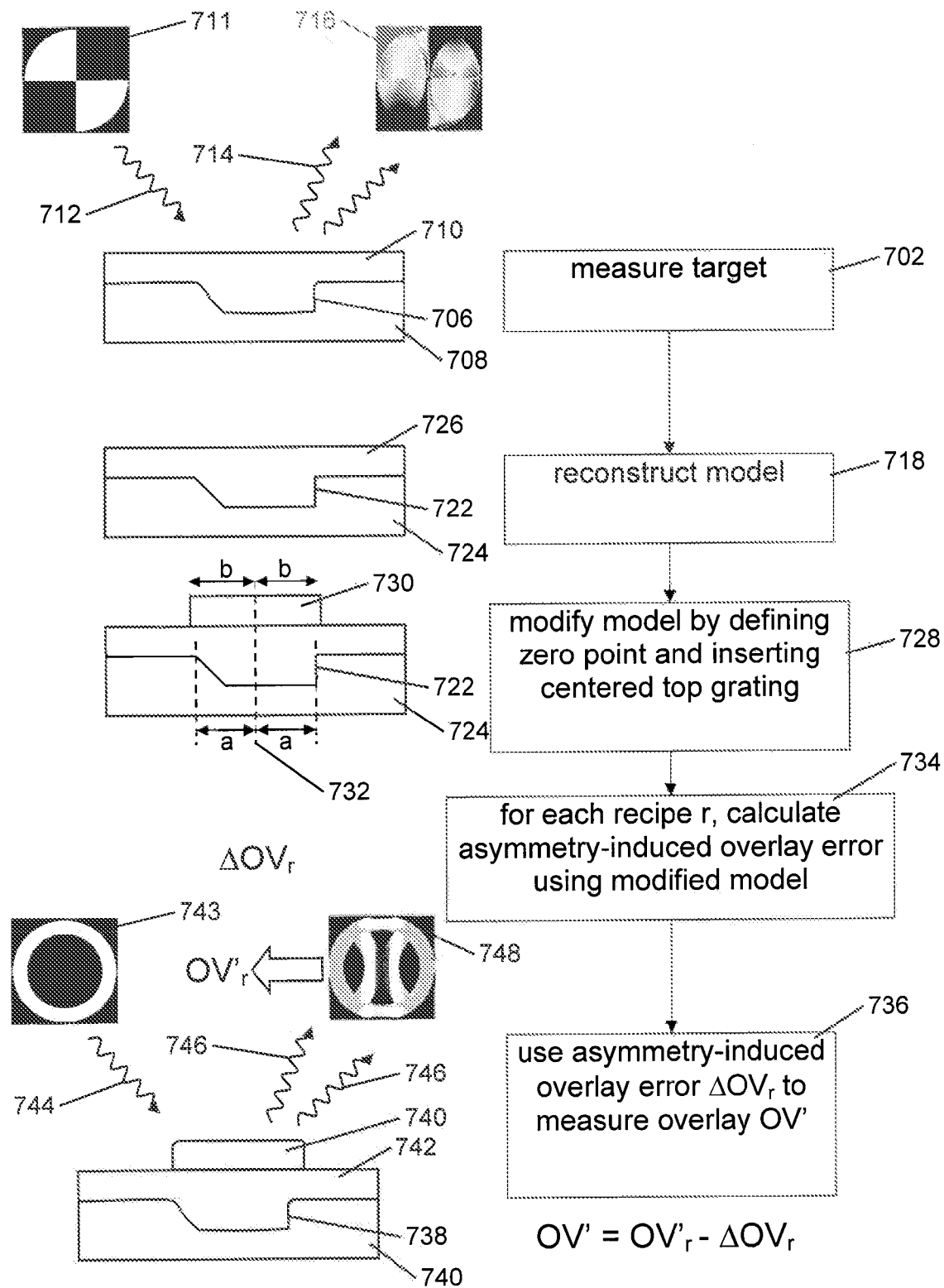
FIG. 7 depicts a method of determining an overlay error in accordance with an embodiment of the present invention illustrating positioning of a centered top grating in the model.

FIG. 7 depicts a method of determining an overlay error in accordance with an embodiment of the present invention illustrating positioning of a centered top grating in the model.

In step 702: The scattering properties of a target on a wafer are measured. The measured target comprises a first structure 706, such as a processed grating, which is formed in layers 708 and 710. Structure 706 has process-induced asymmetric distortion, with, in this example, a side wall at the left side that has a shallower slope than the side wall at the right side. Using a scatterometer, such as SM2 described with reference to FIG. 4, the target is illuminated with an illumination profile 711 (for example using an aperture) of radiation 712. The scattered radiation 714 is detected in the pupil plane to obtain an angular resolved spectrum 716. The illumination profile 711 is such that at least one characteristic of the target can be reconstructed using the separately detected zeroth diffracted order and a higher diffracted order. As can be seen in the resolved spectrum 716, the first order diffraction pattern is depicted in the two quadrants (top right and bottom left) corresponding to the dark quadrants in the illumination profile and the zeroth order (reflected) diffraction pattern is depicted in the other two quadrants. The diffraction orders are therefore separated, without the disadvantage of a conventional annular profile which leads to part of the first diffraction order being mixed up in the pupil pane with the zeroth order. Annular illumination profiles can lead to errors in measured target asymmetry since annular illumination provides less information in the diffracted light. For example, in annular illumination, there are no light beams near normal incidence that contain information useful for measuring target asymmetry.

In step 718: A model of the target is constructed, using a modeling process as described with reference to FIGS. 5 and 6. The model structures 722 to 726 correspond to the target structures 706 to 710 respectively. The processed overlay target is thus reconstructed including its asymmetric distortion.

In step 728: The model is modified based on asymmetry of the first model structure 722. This involves defining a positional parameter, in this example the center point, of the first model structure 722, to compensate for its asymmetry. The "0" position (i.e., the "center") 732 of the processed reconstructed grating is defined. The semiconductor device manufacturer (i.e., the end-user) can give input to define this center position 732 based on a physical explanation or model of the process or other methods such as correlation to electrical overlay measurements or device yield. The center 732 may be defined for example with knowledge of the intended structure shape (without any process-induced asymmetry).

Figure 8:
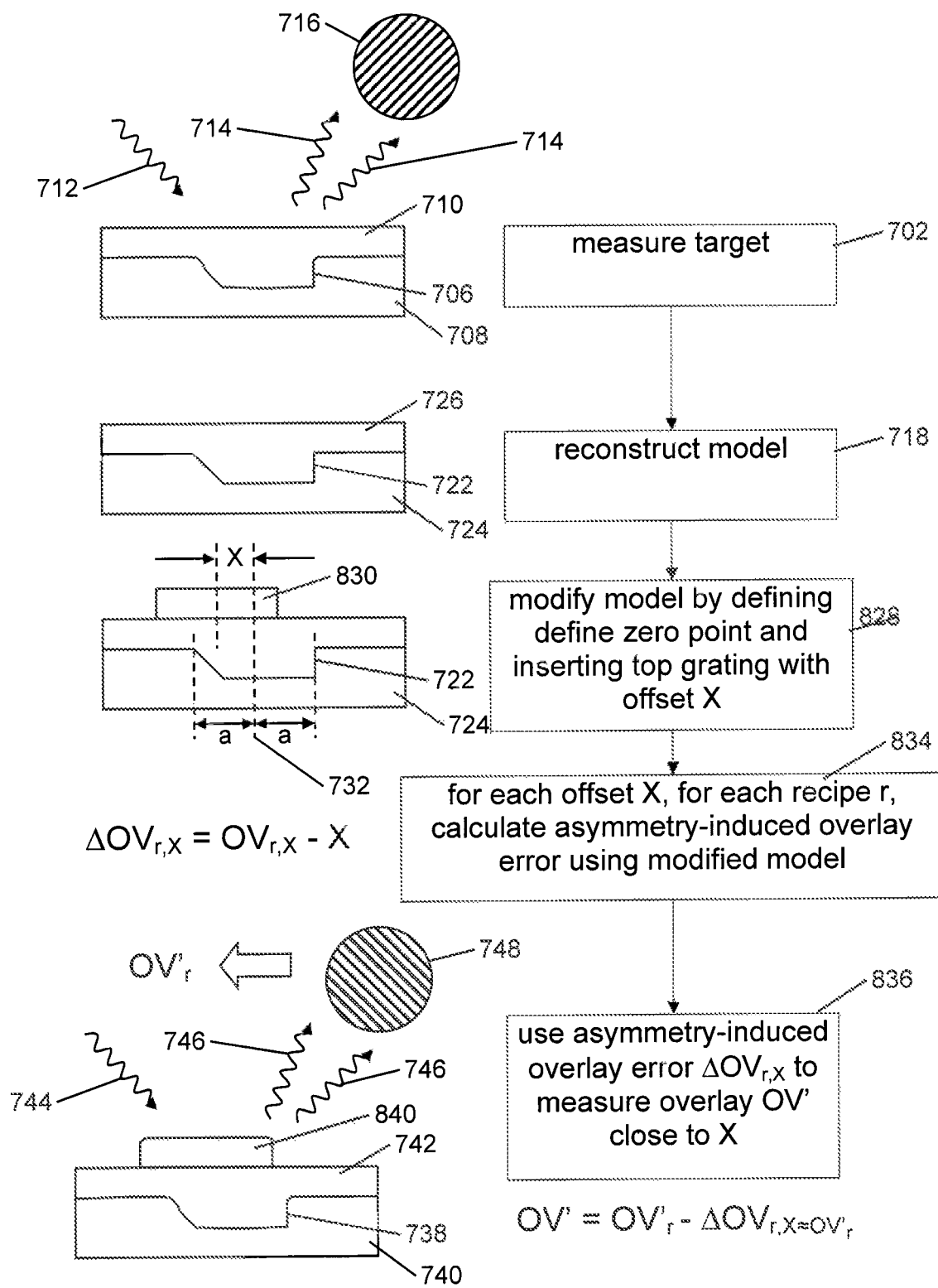
FIG. 8 depicts a method of determining an overlay error in accordance with an embodiment of the present invention illustrating positioning of an offset top grating in the model.
Figure 9:
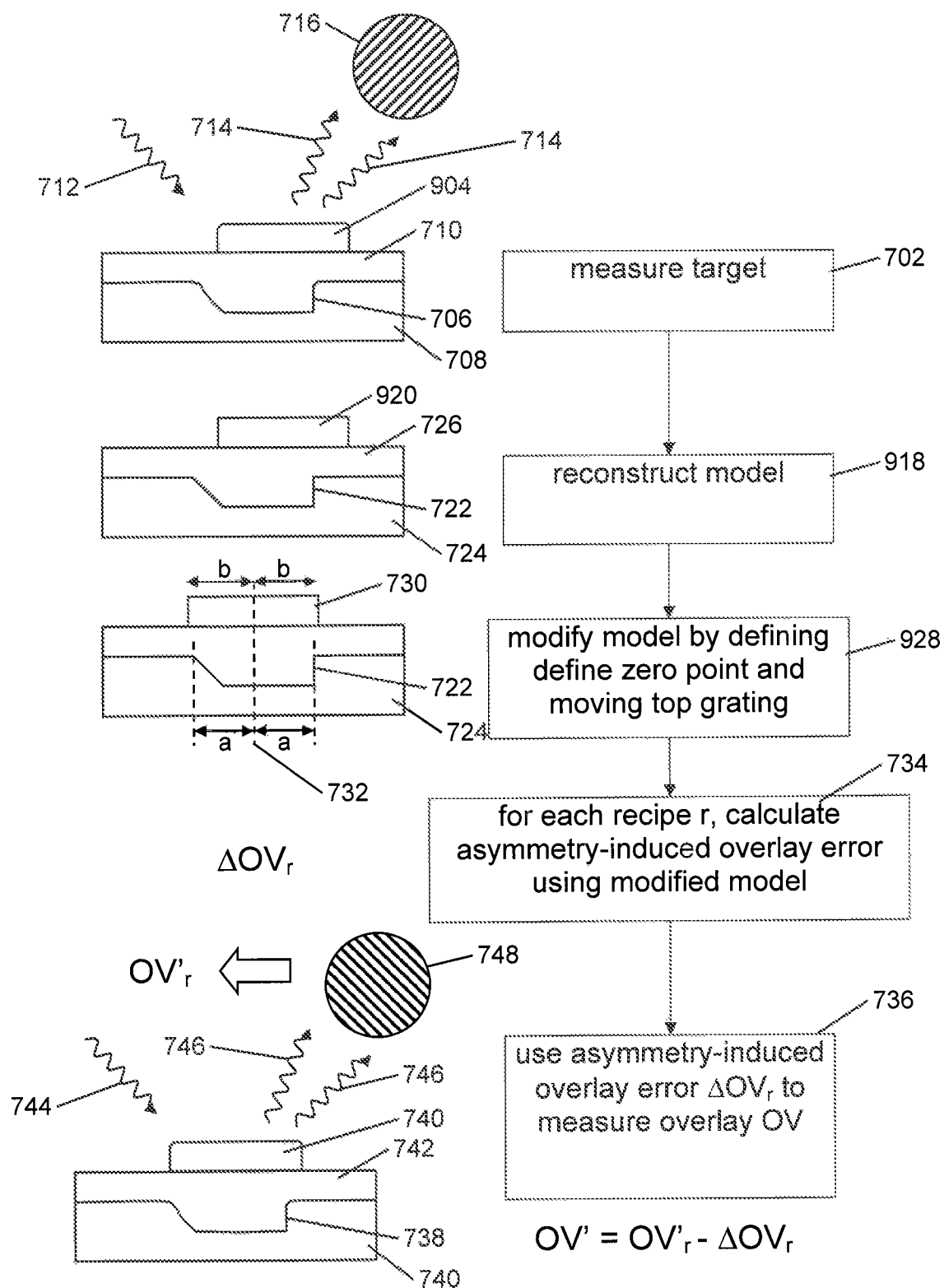
FIG. 9 depicts a method of determining an overlay error in accordance with an embodiment of the present invention illustrating measurement and reconstruction of both the bottom and top gratings.
Figure 10:
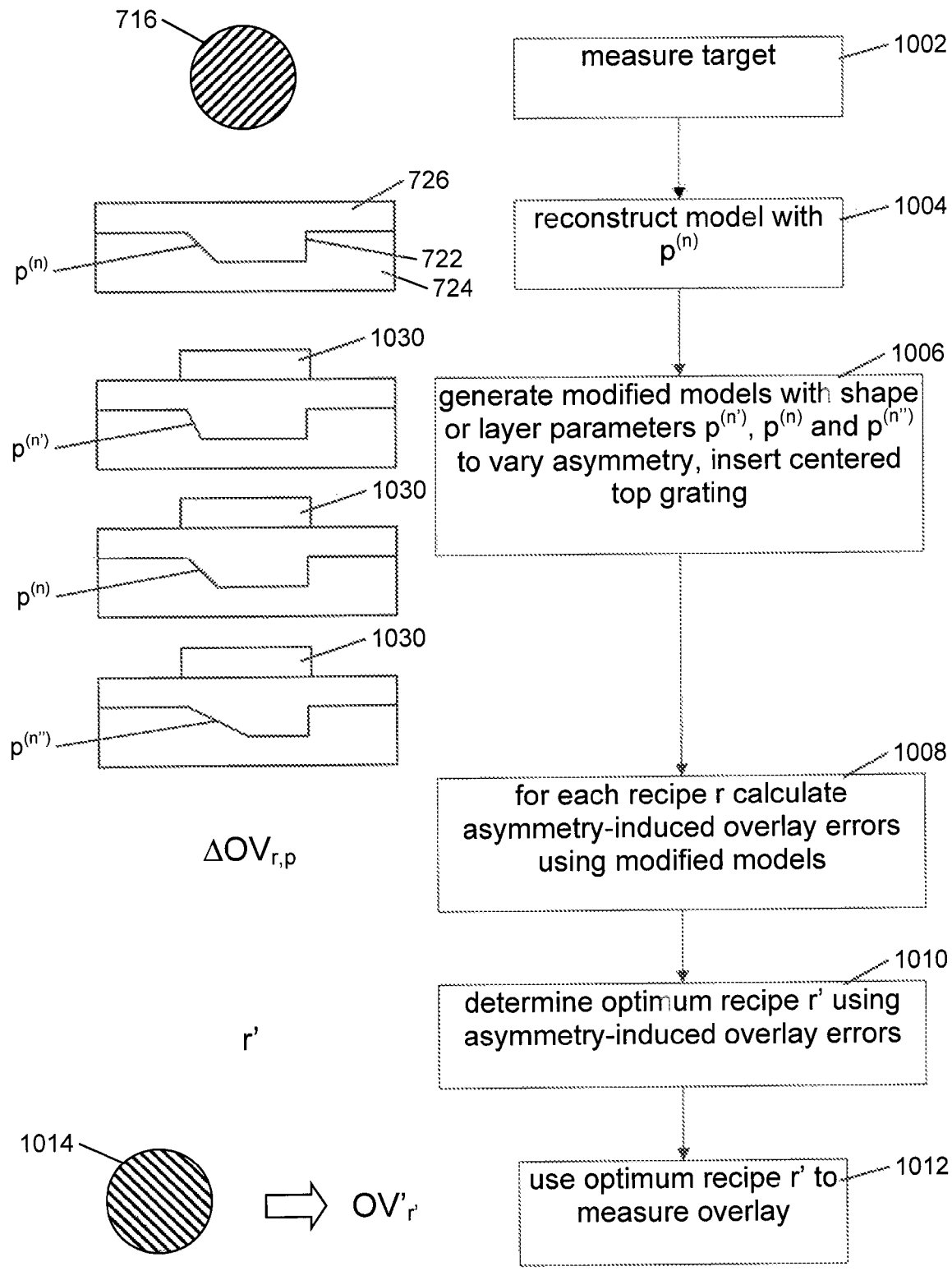
FIG. 10 depicts a method of determining an overlay error in accordance with an embodiment of the present invention illustrating varying modeled asymmetry to determine an optimum recipe.
Figure 11:
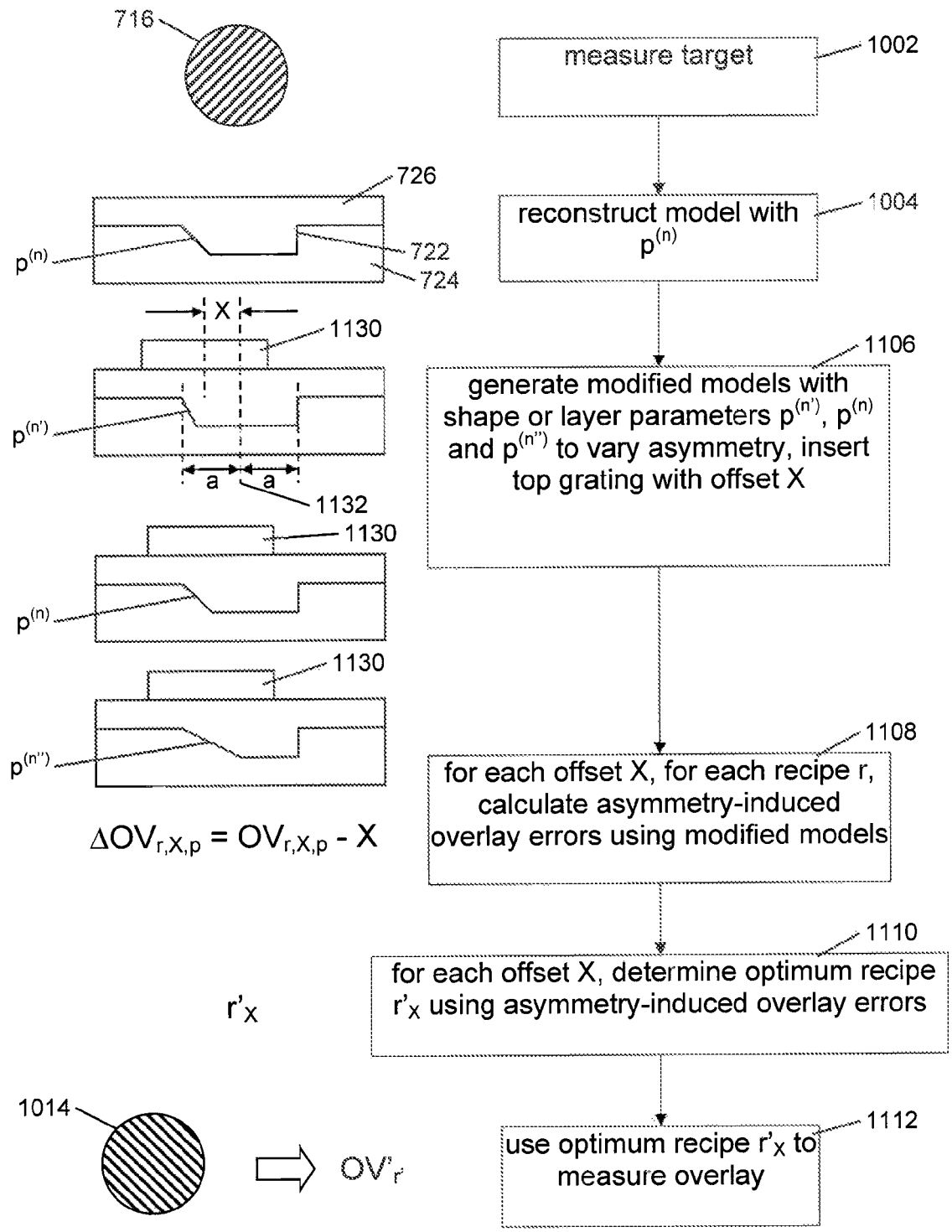
FIG. 11 depicts a method of determining an overlay error in accordance with an embodiment of the present invention illustrating varying modeled asymmetry to determine an optimum recipe for large overlay errors.

In this embodiment, the second model structure 730, representing a resist grating in this example, is introduced to the model at this stage. The first model structure 722 and a second model structure 730 are positioned relative to each other using the positional parameter. This is achieved in FIG. 7 by inserting (but may also be done by moving, as shown in FIG. 9) the position in the model of one or both of the model structures 722 and 730. This positioning may overlay the model structures so that they are centered with respect to each other (FIGS. 7, 9 and 10). Alternatively the model structures 722 and 730 may be positioned relative to each other with a deliberate offset, X (FIGS. 8 and 11).

In analysis software the resist grating 730 is inserted and placed on the reconstructed process stack in such a way that the resist grating 730 is centered on top of the center 732 of the processed grating 722 (i.e., the overlay error is zero). This may be performed entirely in software, so no real experiments are needed. As shown in FIG. 7, the position has been adjusted such that the center of the top structure 730, in between arrows b, is at the same position as the center 732 of the underlying structure 722, in between arrows a. In FIG. 7, the width of the upper model structure 730, b+b, is the same as the width of the lower model structure 722 (without any process-induced asymmetry), a+a. However, it will be appreciated that the widths may be different, i.e., a≠b.

In step 734: An asymmetry-induced overlay error $\Delta OV_r$ between the first 722 and second 730 model structures is determined using the modified model. The asymmetry-induced overlay error may be calculated as an intensity delta in the pupil plane between plus and minus first diffraction orders, as determined at pixels across the detector in the pupil plane. Pixels may be identified in the pupil plane that have relatively large asymmetry-induced overlay errors for even small amount of asymmetries. These pixels may be excluded from the calculation of the asymmetry-induced overlay error number for the whole pupil plane, $\Delta OV_r$, in step 736 below.

The asymmetry-induced overlay error may be calculated by a numerical calculation to simulate a scatterometer overlay measurement on the modified model. Such a measurement is disclosed in US Patent Publication 2006/0033921 A1, which is incorporated by reference herein in its entirety. Typically, this is repeated for several scatterometer measurement recipes r so that a set of corrections $\Delta OV_r$ are prepared for subsequent use with the different recipes, for example with different combinations of illumination wavelengths and polarizations. This asymmetry-induced overlay error $\Delta OV_r$ is the correction that is subsequently applied to overlay measurements during semiconductor device production, as described in the next step 736.

In step 736: The measured (uncorrected) overlay error $OV'_r$ is obtained using recipe r in a scatterometer, such as SM2 described with reference to FIG. 4, to measure an angular-resolved spectrum 748 of a second target, such as on a production semiconductor wafer. The measured second target comprises a first structure 738, such as a processed grating, which is formed in layers 740 and 742. Structure 738 has process-induced asymmetric distortion similar to that of structure 706. Using a scatterometer, such as SM2 described with reference to FIG. 4, the target is illuminated with an illumination profile 743 of radiation 744. The scattered radiation 746 is detected to obtain an angular resolved spectrum 748. The annular illumination profile 743 is suitable for a diffraction-based overlay measurement method to be used, such as disclosed in US Patent Publication 2006/0033921 A1. That method does not include any reconstruction, so is fast enough for production wafers, but is degraded by asymmetry in the underlying processed grating and it is desirable to correct for this asymmetry.

The corrected overlay error OV' is determined by calculating the difference between the asymmetry-induced overlay error $\Delta OV_r$ and a measured overlay error $OV'_r$ of the second target. Thus, corrected overlay error $OV'=OV'_r-\Delta OV_r$.

The overlay correction may be calculated using a calculated overlay number $OV'_r$ taking all pixels at coordinates x and y in the measurement pupil plane into account, i.e., $$OV' = \sum_{x,y} OV'_{r,x,y} - \sum_{x,y} \Delta OV_{r,x,y}.$$

Alternatively, an overlay correction for every pixel can be calculated first individually and then the net overlay error calculated by averaging the overlay over all pixels, i.e., $$OV' = \sum_{x,y} (OV'_{r,x,y} - \Delta OV_{r,x,y}).$$

For the measurement of the overlay error OV' in the second target, the optimum recipe r' may be determined and selected to be used for this step in accordance with the embodiment described below with reference to FIGS. 10 and 11.

Since the target shape will vary over a wafer, steps 702, 718, 728 and 734 and 736 may be performed for every target on the wafer or a representative subset of targets.

This embodiment has the effect of reducing processing variations in semiconductor manufacturing and ultimately helps to improve overlay. This, in turn, increases semiconductor manufacturing yield.

These calculations of the asymmetry-induced overlay error $\Delta OV_r$ for different measurement recipes r may be performed for centered gratings as described with reference to FIG. 7, which is useful to correct measurements of overlay errors close to zero, where $OV'_r=0$. However, for measuring large overlay errors $OV'_r \approx X$ it is useful to calculate this asymmetry-induced overlay error around the measured overlay error X, that is $\Delta OV_{r,X \sim OV'r}$. Therefore the corrected overlay error is $OV'=OV'_r-\Delta OV_{r,X \sim OV'r}$. This is because of the non-linear behavior of diffraction based overlay. The same amount of target asymmetry will give slightly different asymmetry-induced overlay errors for an overlay error near zero compared to a large overlay error. This approach is described with reference to FIGS. 8 and 11.

FIG. 8 depicts a method of determining an overlay error in accordance with an embodiment of the present invention illustrating positioning of an offset top grating in the model. In FIG. 8, numerals the same as in FIG. 7 correspond to the same steps and objects. However, in FIG. 8, in step 828 the model is modified by inserting the second model structure 830, which represents the top resist grating, on the reconstructed process stack in such a way that the resist grating 830 is offset by a distance X from the center 732 of the processed grating 722 (i.e., the overlay error is X).

This may be repeated for several values of X to build a library or lookup table of asymmetry-induced overlay errors for a range of offsets X. X may be equal to 0, which is equivalent to the case illustrated by FIG. 7. In step 834 an asymmetry-induced overlay error $\Delta OV_{r,X}$ between the first 722 and second 830 model structures is determined using the modified model for each of the values of X.

In FIG. 8 the top product grating structure 840 is shown having an offset of approximately X from the underlying product grating 738. Step 836 is the same as for step 736 except the value of asymmetry-induced overlay error is selected to match the measured overlay error X, that is $\Delta OV_{r,X \sim OV'r}$, then as described above, the corrected overlay error becomes $OV'=OV'_r-\Delta OV_{r,X \sim OV'r}$.

FIG. 9 depicts a method of determining an overlay error in accordance with an embodiment of the present invention illustrating measurement and reconstruction of both the bottom and top gratings. In FIG. 9, numerals the same as in FIG. 7 correspond to the same steps and objects. However, in FIG. 9 the unit cell of the first target is shown in cross section with a resist structure 904, such as a resist grating, overlaid on the processed structure 706.

In step 918 a model of the target is constructed, using a modeling process as described with reference to FIGS. 5 and 6. The model structure 920 corresponds to the target structure 904. In step 928 the model is modified such that the first model structure 722 and a second model structure 730 are positioned relative to each other using the positional parameter. This is achieved in FIG. 9 by moving the position in the model of the model structure 920 to position 730. This movement overlays the model structures so that they are centered with respect to each other. Alternatively the model structures 722 and 730 may be positioned relative to each other with a deliberate offset X as discussed with reference to FIG. 8.

Alternatively, instead of moving any model structure, modifying the model may be performed by adjusting an overlay parameter used to model overlay error between the model structures 722 and 920. Therefore the positions of model structures remain unchanged in the model.

FIG. 10 depicts a method of determining an overlay error in accordance with an embodiment of the present invention illustrating varying modeled asymmetry to determine an optimum recipe.

In step 1002: The scattering properties of a target on a wafer (not shown) are measured. As discussed with reference to FIG. 7, an angular resolved spectrum 716 is obtained using a scatterometer.

In step 1004: As described with reference to FIG. 7, a model of the target is constructed. The geometric parameter $p^{(n)}$ is a parameter of the model structure 722 corresponding to the shape of the lower target structure 706 in FIG. 7. In particular, p" is a shape parameter that describes the asymmetry of the lower model structure 722. In this example $p^{(n)}$ specifies a particular sidewall slope angle. Another type of geometric parameter is a layer thickness parameter. Instead of, or in addition to, a geometric parameter, the model structure parameter may comprise a material parameter that affects radiation scattering.

In the following steps 1006 and 1008, models of the reconstructed shape and its (expected) variations are fed into a forward calculator to calculate asymmetry-induced overlay errors.

In step 1006: The model is modified based on asymmetry of the underlying model structure 722. In this embodiment, this involves adjusting parameter $p^{(n)}$ to different values $p^{(n')}$ and $p^{(n'')}$ to vary asymmetry in the model structure and therefore to vary the asymmetry-induced overlay error between the lower model structure 722 and an inserted upper model structure 1030. In this example, $p^{(n')}$ and $p^{(n'')}$ correspond to different specific sidewall slope angles.

In step 1008: For each modified model, with parameters $p^{(n')}$ and $p^{(n'')}$, and for the original model, with parameter $p^{(n)}$, calculation of an asymmetry-induced overlay error $\Delta OV_{r,p}$ is repeated for several scatterometer measurement recipes, r. The calculations are performed using the modified models in a numerical calculation to simulate a scatterometer overlay measurement on each modified model.

In step 1010: An overlay error OV in a production target is determined by first using the calculated asymmetry-induced overlay errors $\Delta OV_{r,p}$ to select an optimum scatterometer measurement recipe r' used to measure the production target, for example with the optimum wavelength and polarization. The recipe showing the most stable behavior to these model variations is selected as being the optimal recipe r'. Stable behavior may be determined as low sensitivity to the model shape parameter variation. Context information may be used in analyzing the variation, for example if a line is to be placed on top of a contact, it is important to focus on measurements of scattering by the top of the profile to select the recipe that gives an optimal result.

In step 1012: The measured overlay error $OV'_{r'}$ is obtained using a scatterometer, such as SM2 described with reference to FIG. 4, using optimum recipe r', as determined in step 1010, to measure an angular-resolved spectrum 1014.

The embodiment described with reference to FIGS. 10 and 11 may be combined with the embodiments described with reference to FIGS. 7 to 9. For example the optimum recipe r' determined as described with reference to FIG. 10 can be used to measure the product overlay and then an asymmetry-induced overlay error may be subtracted from the measured product overlay error as described with reference to FIG. 7.

FIG. 11 depicts a method of determining an overlay error in accordance with an embodiment of the present invention illustrating varying modeled asymmetry to determine an optimum recipe for large overlay errors. In FIG. 11, numerals the same as in FIG. 10 correspond to the same steps and objects. However in step 1106 upper model structure 1130 is inserted with an offset X, for the same purpose as discussed with reference to FIG. 8. Furthermore in step 1108 the calculations of the asymmetry-induced overlay errors are performed for each offset X, for each recipe r. Consequently, in step 1110 the optimum recipe can be determined for each offset X. Finally in step 1112, a measurement on a product wafer using a non-optimum recipe can provide a course value of the overlay error. Then the optimum recipe with an offset X matching the course measured product overlay error can be selected to perform the measurement on the same or subsequent targets expected to have the same product overlay error.

The embodiments of the present invention described with reference to FIGS. 10 and 11 provide a robust way of selecting scatterometer measurement recipes. Using these embodiments of the present invention avoids increased process complexity and cost and time of production when using overlay targets of reference layers with asymmetrical profiles.

The methods according to embodiments of the present invention may be implemented in the processor PU of the scatterometer SM2 in FIG. 4 by executing a computer program product containing one or more sequences of machine-readable instructions to cause one or more processors to perform the methods described herein.

The scatterometer may be a stand-alone inspection apparatus or may be incorporated into the lithography apparatus LA or lithographic cell LC of FIGS. 1 and 2 respectively.

Although specific reference may be made in this text to the use of methods and apparatus in the manufacture of ICs, it should be understood that the inspection methods and apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents The descriptions above are intended to be illustrative, not limiting. Thus, it will be apparent to one skilled in the art that modifications may be made to the present invention as described without departing from the scope of the claims set out below.

The invention claimed is:

1. A method comprising:
    measuring scattering properties of a first target comprising a first structure having an asymmetric distortion;
    constructing a model of the first structure using the measured scattering properties, the model being a parameterized model that reconstructs the shape of first structure and the asymmetric distortion;
    modifying the model based on the asymmetric distortion of the reconstructed first structure;
    calculating an asymmetry-induced overlay error between the reconstructed first structure and a second model structure, the reconstructed first structure and the second model structure being overlaid with respect to each other in the modified model; and determining an overlay error in a second target using the calculated asymmetry-induced overlay error.

2. The method of claim 1, wherein the modifying the model further comprises the steps of:

defining a positional parameter of the first model structure to compensate for the asymmetric distortion; and positioning the reconstructed first structure and the second model structure relative to each other using the defined positional parameter.

3. The method of claim 2, wherein the positioning comprises adjusting the position in the model of at least one of the reconstructed first structure and the second model structure.

4. The method of claim 2, wherein the positioning comprises inserting the second model structure in the model.

5. The method of claim 2, wherein the determining an overlay error in a second target comprises calculating the difference between the asymmetry-induced overlay error and a measured overlay error of the second target.

6. The method of claim 2, wherein defining the positional parameter of the first model structure to compensate for the asymmetric distortion comprises defining a center point of the reconstructed first structure based on information about a device being manufactured.

7. The method of claim 1, wherein the modifying comprises adjusting an overlay parameter used to model overlay error between the reconstructed first structure and the second model structure.

8. The method of claim 1, wherein the first target comprises a second structure;

wherein the parameterized model reconstructs the shape of second structure; and wherein the second model structure corresponds to the second structure.

9. The method of claim 1, wherein the parameterized model reconstructs a material property of the first structure.

10. The method of claim 9, wherein the parameterized model comprises at least one of a geometric parameter and a material parameter.

11. A method comprising:

measuring scattering properties of a first target comprising a first structure;

constructing a model of the first structure using the measured scattering properties, the model comprising a first model structure corresponding to the first structure;

modifying the model based on asymmetry of the first model structure;

calculating an asymmetry-induced overlay error between the first model structure and a second model structure, the first and second model structures being overlaid with respect to each other in the modified model; and determining an overlay error in a second target using the calculated asymmetry-induced overlay error;

wherein the modifying the model comprises adjusting a model structure parameter value to vary the asymmetry-induced overlay error;

wherein the calculating an asymmetry-induced overlay error is repeated for a plurality of model structure parameter values for a plurality of scattering property measurement recipes; and wherein the determining an overlay error in the second target comprises using the calculated asymmetry-induced overlay errors to select an optimum scattering property measurement recipe used to measure the second target.

12. The method of claim 11, wherein the parameter comprises a geometric parameter.

13. The method of claim 11, wherein the parameter comprises a material parameter.

14. The method of claim 11, wherein the model structure parameter models asymmetry of the first model structure.

15. A method comprising:

measuring scattering properties of a first target comprising a first structure;

constructing a model of the first structure using the measured scattering properties, the model comprising a first model structure corresponding to the first structure;

modifying the model based on asymmetry of the first model structure;

calculating an asymmetry-induced overlay error between the first model structure and a second model structure, the first and second model structures being overlaid with respect to each other in the modified model; and determining an overlay error in a second target using the calculated asymmetry-induced overlay error;

wherein the first target comprises a second structure, the first and second structures being overlaid with respect to each other, and the second model structure corresponds to the second structure.

16. A method comprising:

measuring scattering properties of a first target comprising a first structure;

constructing a model of the first structure using the measured scattering properties, the model comprising a first model structure corresponding to the first structure;

modifying the model based on asymmetry of the first model structure;

calculating an asymmetry-induced overlay error between the first model structure and a second model structure, the first and second model structures being overlaid with respect to each other in the modified model; and determining an overlay error in a second target using the calculated asymmetry-induced overlay error;

wherein the calculating an asymmetry-induced overlay error comprises calculating an overlay error at a plurality of pixels in a pupil plane of an angular resolved scatterometer while excluding pixels that have the largest overlay errors in response to the asymmetry of the first model structure.

17. An inspection apparatus for determining an overlay error and configured to measure scattering properties of a first target comprising a first structure having an asymmetric distortion, the inspection apparatus comprising:

at least one processor configured to:

construct a model of the first structure using the measured scattering properties, the model being a parameterized model that reconstructs the shape of first structure and the asymmetric distortion;

modify the model based on the asymmetric distortion of the reconstructed first structure;

calculate an asymmetry-induced overlay error between the reconstructed first structure and a second model structure, the reconstructed first structure and the second model structure being overlaid with respect to each other in the modified model; and determining an overlay error in a second target using the calculated asymmetry-induced overlay error.

18. A lithographic apparatus comprising:

an illumination optical system arranged to illuminate a pattern;

a projection optical system arranged to project an image of the pattern on to a substrate; and an inspection apparatus for determining an overlay error, the inspection apparatus configured to measure scattering properties of a first target comprising a first structure having an asymmetric distortion, the inspection apparatus comprising:
at least one processor configured to:
construct a model of the first structure using the measured scattering properties, the model being a parameterized model that reconstructs the shape of first structure and the asymmetric distortion;
modify the model based on the asymmetric distortion of the reconstructed first structure;
calculate an asymmetry-induced overlay error between the reconstructed first structure and a second model structure, the reconstructed first structure and the second model structure being overlaid with respect to each other in the modified model; and
determine an overlay error in a second target using the calculated asymmetry-induced overlay error.

19. A lithographic cell comprising:
a coater arranged to coat substrates with a radiation sensitive layer;
a lithographic apparatus arranged to expose images onto the radiation sensitive layer of substrates coated by the coater;
a developer arranged to develop images exposed by the lithographic apparatus; and
an inspection apparatus for determining an overlay error, the inspection apparatus configured to measure scattering properties of a first target comprising a first structure having an asymmetric distortion, the inspection apparatus comprising:
at least one processor configured to:
construct a model of the first structure using the measured scattering properties, the model being a parameterized model that reconstructs the shape of first structure and the asymmetric distortion;
modify the model based on the asymmetric distortion of the reconstructed first structure;
calculate an asymmetry-induced overlay error between the reconstructed first structure and a second model structure, the reconstructed first structure and the second model structure being overlaid with respect to each other in the modified model; and
determine an overlay error in a second target using the calculated asymmetry-induced overlay error.

20. A non-transitory computer readable medium comprising one or more sequences of machine-readable instructions for determining an overlay error, the instructions being adapted to cause one or more processors to perform a method of determining an overlay error, the method comprising:
measuring scattering properties of a first target comprising a first structure having an asymmetric distortion;
constructing a model of the first structure using the measured scattering properties, the model being a parameterized model that reconstructs the shape of first structure and the asymmetric distortion;
modifying the model based on the asymmetric distortion of the reconstructed first structure;
calculating an asymmetry-induced overlay error between the reconstructed first model structure and a second model structure, the reconstructed first structure and the second model structure being overlaid with respect to each other in the modified model; and
determining an overlay error in a second target using the calculated asymmetry-induced overlay error.

\* \* \* \* \*

UNITED STATES PATENT AND TRADEMARK OFFICE
CERTIFICATE OF CORRECTION

Page 1 of 1

PATENT NO. : 8,908,147 B2
APPLICATION NO. : 13/181932
DATED : December 9, 2014
INVENTOR(S) : Den Boef et al.

It is certified that error appears in the above-identified patent and that said Letters Patent is hereby corrected as shown below:

In the Claims

Column 22, line 28, claim 20, after "first", please delete "model".

Signed and Sealed this
Seventh Day of July, 2015

Michelle K. Lee
*Director of the United States Patent and Trademark Office*